United States Patent [19]

Zick

[11] 4,312,332
[45] Jan. 26, 1982

[54] OXYGEN SENSING

[75] Inventor: Gregory L. Zick, Kirkland, Wash.

[73] Assignee: Cordis Corporation, Miami, Fla.

[21] Appl. No.: 143,928

[22] Filed: Apr. 25, 1980

[51] Int. Cl.³ .............................................. A61B 5/00
[52] U.S. Cl. .................................... 128/635; 29/61 L;
 128/303.1; 128/637; 204/195 B; 73/1 G
[58] Field of Search ................. 128/2 E, 2.1 E, 303.1;
 29/612; 204/195 R, 195 B, 195 P; 73/1 G

[56] References Cited

U.S. PATENT DOCUMENTS

| 3,662,745 | 5/1972 | Cosentino | 128/2 E |
| 3,678,375 | 10/1978 | McFarland | 204/195 P |
| 3,794,575 | 2/1974 | Niedrach et al. | 204/195 P |
| 3,795,239 | 3/1974 | Eberhard et al. | 128/2 E |

OTHER PUBLICATIONS

IEEE Transactions on Parts, Materials and Packaging, vol. PMP-5; No. 2, Jun. 1969–*Organic Thin Film Capacitor*, Paul J. Ozawa.

*Enhancing Oxygen Electrode Stability with Plasma Polymerized Coatings*–Allen W. Hahn et al.
*Adhesion and Hydrophilicity of Glow–Discharge–Polymerized Propylene Coatings;* "Journal Applied Physics" vol. 49, No. 10, Oct. 1978.
*Cold Plasma Polymerized Films and Their Biomedical Applications* Kenneth G. Mayhan & Allen W. Hahn, 24th ACEMB–Int. Hotel Las Vegas, Nevada 10-31 to 11-4-71.

*Primary Examiner*—Leon Gilden
*Attorney, Agent, or Firm*—Kenway & Jenney

[57] ABSTRACT

Oxygen sensing as disclosed herein is performed by applying a solid state, self-heating sensor to the patient's skin. A noble metal cathode and a thick-film reference electrode are provided on the front face of a thin flat substrate employed in the sensor. A thick-film resistive heater is provided on the back surface of the substrate for heating the sensor to produce hyperemia in the adjacent tissue so that a polarographic measurement of oxygen concentration may be obtained by means of the electrodes on the front face.

8 Claims, 8 Drawing Figures

OXYGEN SENSING

BACKGROUND OF THE INVENTION

This invention relates to the sensing of oxygen and, more particularly, to a system for measuring the partial pressure of oxygen in a patient's blood.

It has previously been proposed to obtain a transcutaneous measurement of the partial pressure of oxygen in blood by utilizing a so-called Clark type electrode, i.e. an electrode in which a polarographic anode and cathode are immersed in an electrolyte which is interfaced to the environment in which oxygen to be sensed through an oxygen permeable membrane. One such arrangement is disclosed in U.S. Pat. No. 3,795,239 issued to Eberhard et al.

While such prior art units have, to some extent, been successful, the units must be reassembled and allowed to stabilize prior to each use and must likewise be calibrated prior to each use. In addition to this considerable effort which must be gone through each time the apparatus is to be used, the necessary bulk of the electrode system, together with the typical use of a separate heating element, has meant that tight temperature regulation has not been obtainable. Furthermore, the devices have been quite expensive and so bulky and heavy as to interface with their easy application to a patient. Likewise, their cost was such that the medically preferred single use or a throw away type of construction was not feasible.

The oxygen sensor is usually heated by means of a separate heater mounted on the electrode. Often a separate, non-integral temperature sensor is also attached to the electrode. The temperature sensor is used with an external automatic control loop to control the temperature of the sensor very accurately. A high degree of accuracy in temperature regulation is desirable so that the level of oxygen perfusing through the skin is a good indication of arterial blood oxygen partial pressure. In the past, typical oxygen sensing electrodes have been made by machining and molding. Electrodes made in this way have several disadvantages. First, such electrodes are costly in that the manufacture is highly labor intensive; and, second, these electrodes traditionally have poor temperature regulation capability and are bulky and heavy in weight.

Among the several objects of the present invention may be noted a provision of an oxygen measuring system which provides accurate measurement; the provision of such a system which is adapted for oxygen measurement transcutaneously; the provision of such a system providing precise temperature regulation; the provision of such a system in which the sensing elements can be easily applied to a patient; the provision of such a system which can be manufactured relatively inexpensively and in a manner well-suited to high volume production; the provision of such a system in which the electrodes applied to the patient are smaller and lighter in weight than previous electrodes and are inexpensive enough to be disposable. Other objects and features will be in part apparent and, in part, pointed out hereinafter.

SUMMARY OF THE INVENTION

The objects of the invention are obtained largely by providing an essentially solid state electrode system in which many of the operative elements of the system are formed on the front and back surfaces of a thin ceramic substrate using thick film printed circuit techniques.

In accordance with preferred practice of the the invention, a thin flat substrate is provided having front and back surfaces, the front surface being adapted to contact a patient's skin. A noble metal cathode extends through the substrate to the front surface where a limited area is exposed for reducing oxygen. A reference electrode comprising a silver/silver chloride composite in a fusible binder is formed on the front surface adjacent the cathode. A resistor is printed onto the back surface of the substrate for heating the substrate. A polymer coating, formed in situ by plasma polymerization, is provided over the front surface of the substrate, including the electrodes.

Feedback control means are provided for energizing the resistor to heat the substrate to a predetermined temperature suitable for producing hyperemia in the adjacent tissue of a patient to whom the substrate is supplied. Circuit means are also employed for applying a potential between the cathode and the reference electrode and for measuring the resultant current, the current so measured being a function of the oxygen content of the patient's blood.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
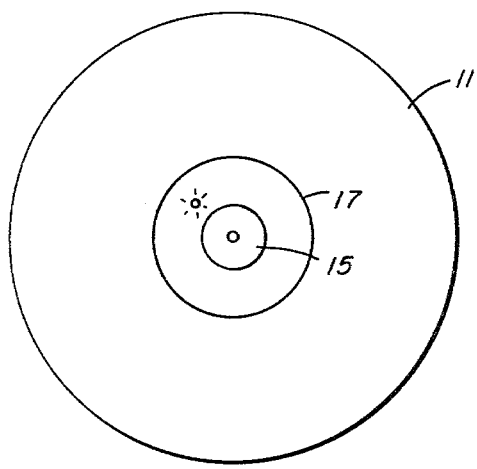
FIG. 1 is a front face view of a solid state sensor employed in an oxygen sensing system of the present invention.
Figure 2:
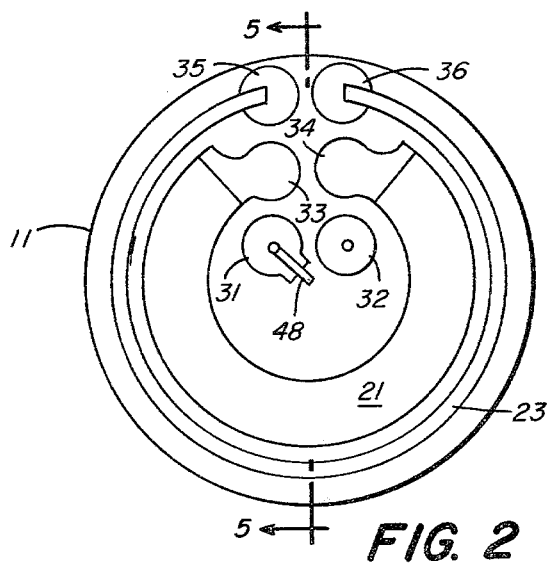
FIG. 2 is a back view of the sensor of FIG. 1.

Referring now to FIG. 1, the sensing portion of the system employs a thin, flat substrate 11, the front surface of which is adapted to contact the patient's skin. A preferred form of the substrate 11 is a thin disk of aluminum or beryllium oxide. This disk may, for example, be of three-eighths inch diameter and 0.020 inch thick. The front face of the substrate carries a noble metal cathode 15 and a reference electrode 17. As described in greater detail hereinafter, electrodes 15 and 17 comprise a polarographic system for measuring the oxygen content of a patient's blood by the reduction of oxygen at the cathode 15. To improve stability of the polarographic electrode system, at least the front surface of the substrate, together with the electrodes 15 and 17, is covered by a very thin, oxygen and electrolyte permeable polymer coating, formed in situ as described hereinafter.

A circular heating resistor 21 and an annular thermistor 23 are printed on the back of the substrate 11. Conductive pads 31–37 are provided for establishing electrical connection to these resistive elements, as well as to the electrodes 15 and 17 in a manner described hereinafter. Leads (not shown) are attached to the pads 31–37, e.g. by means of conductive epoxy or solder for connection to the control and measurement circuitry, also described hereinafter.

METHOD OF CONSTRUCTING THE OXYGEN SENSOR

Figure 3:
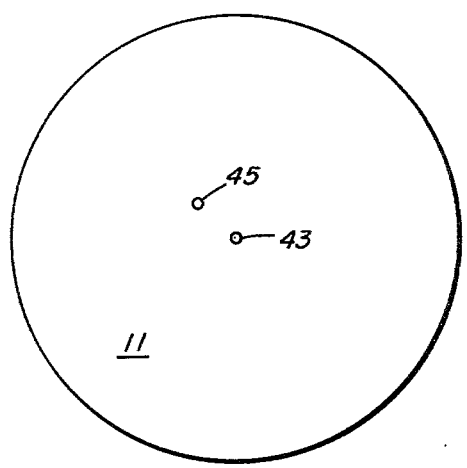
FIG. 3 is a front face view of a thin ceramic disk employed as a substrate in manufacturing the sensor of FIGS. 1 and 2.
Figure 4:
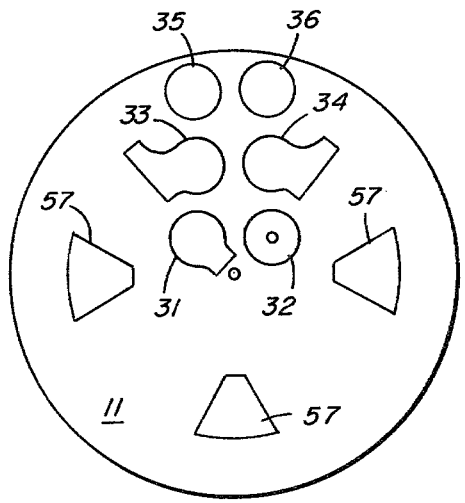
FIG. 4 is a back view of the substrate showing a pattern of conductive elements formed thereon as an early step in the manufacture of the sensor.

As indicated previously, a preferred form of the substrate 11 is a thin disk of beryllium oxide. Aluminum oxide is also suitable. Initially the disk is drilled, as indicated at 43 and 45 in FIG. 3, to provide an aperture (43) through which the noble metal cathode can pass and an aperture (45) facilitating connection to the reference electrode 17. Various conductive elements are then formed on the back surface of the substrate by conventional hybrid circuit construction techniques. In the embodiment shown, these conductive elements include the connection pads 31–36 and a series of wedge-shaped elements 57 which underlie portions of the heating resistor 21. A suitable paste or ink for forming the pads 31–36 and the wedges 57 is ESL-9630 manufactured by ElectroScience Labs. This paste is applied in the desired pattern by conventional screening techniques. After the pattern has been screened onto the back surface of the substrate, it is dried for approximately fifteen minutes at 125° and then fired at 1000° C. for twenty minutes to cure the conductive paste.

After the conductive elements have been applied to the back surface of the substrate, the heater element 25 and the thermistor element 23 are screened onto the backside of the substrate. The presently preferred material for this paste or ink is ESL-2612, again a product manufactured by ElectroScience Labs. This is a thermistor paste, i.e. a composition whose resistance changes significantly with temperature. By constructing the heater of such a composition, it can be employed in a self-sensing feedback control circuit and the thermistor 23 can be used for independent temperature measurement, if desired. Alternately, the separate, though integral, thermistor 23 can be used as the sensing element in the temperature controller. After screening with the thermistor paste, the substrate is dried for fifteen minutes at 125° C. and then fired for 875° C. for twenty minutes.

The purpose of the conductive wedges 57 which underlie the resistive heater 21 is to shunt a portion of the resistive current path near the outer circumference of the circular pattern and thereby reduce the radial nonuniformity of current distribution in the heater.

After the heater and thermistor elements have been formed, the reference electrode 17 is screened onto the front surface. The presently preferred paste or ink used in forming the reference electrode is that disclosed in a copending application filed by myself and Stanley H. Saulson on even date herewith, entitled "Solid State Reference Electrode". While the composition is disclosed and claimed in greater detail in said copending application, it may be noted for the purposes of the present application that the material comprises a mixture of finely divided silver and silver chloride, silver chloride forming about 15–25% of the active component. A fusible binder, preferably a glass frit, is mixed with the silver/silver chloride mixture so that, upon firing of the mixture, the active components are bound tightly to the substrate 11. A volatile binder may be included in the paste itself to facilitate temporary adhesion during the screening process.

After the reference electrode pattern is screened onto the substrate using the paste or ink described above, the substrate is dried for fifteen minutes at 125° C. and then fired at 500° C. for fifteen minutes. (The drying process drives off the volatile binder prior to firing.) The firing process itself fuses the glass frit, binding the chemically active elements in the mixture to the substrate. Though the pattern overlies the aperture 45, the material is not caused to clog this opening or, if it is, the opening is subsequently mechanically reopened. As is conventional in the thin film and hybrid circuit manufacturing arts, the sequence of screening and firing steps is performed so that the progression is from higher firing temperatures to the lower firing temperatures.

An alternative method of forming the reference electrode 17 would be to use a paste containing only the silver component, e.g. ESL-9990 from ElectroScience Labs, and then chloridate the surface using a conventional wet electrolytic process.

Figure 5:
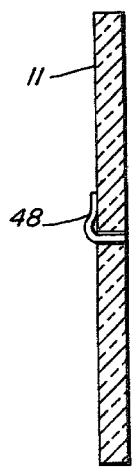
FIG. 5 is a side view, in section, of the sensor, taken substantially on the line 5—5 of FIG. 2.

To form the cathode 15, a short length of three mil. gold wire 48 is bent at essentially right angles. One arm of the right angle is passed through the center hole 43 with the orthogonal portion coming to rest on the conductive pad 31 where it is secured with the conductive epoxy (FIG. 5). The same conductive epoxy may be used to fill the hole 45 establishing a connection between the pad 32 and the reference electrode 17 on the front surface of the substrate. After the epoxy is cured, the wire which will form the cathode is sealed within the hole 43. A suitable material for this is a polyester resin such as Clear Cast. The portion of the gold wire protruding beyond the front surface of the substrate is then shaved off with a sharp scalpel to provide a fresh anodic surface.

After the printed circuit steps are completed, short leads are connected to the various pads 31–36 by means of conductive epoxy and these leads terminate in a connector suitable for electrically coupling the sensor to the control and measurement electronics described hereinafter.

Figure 6:
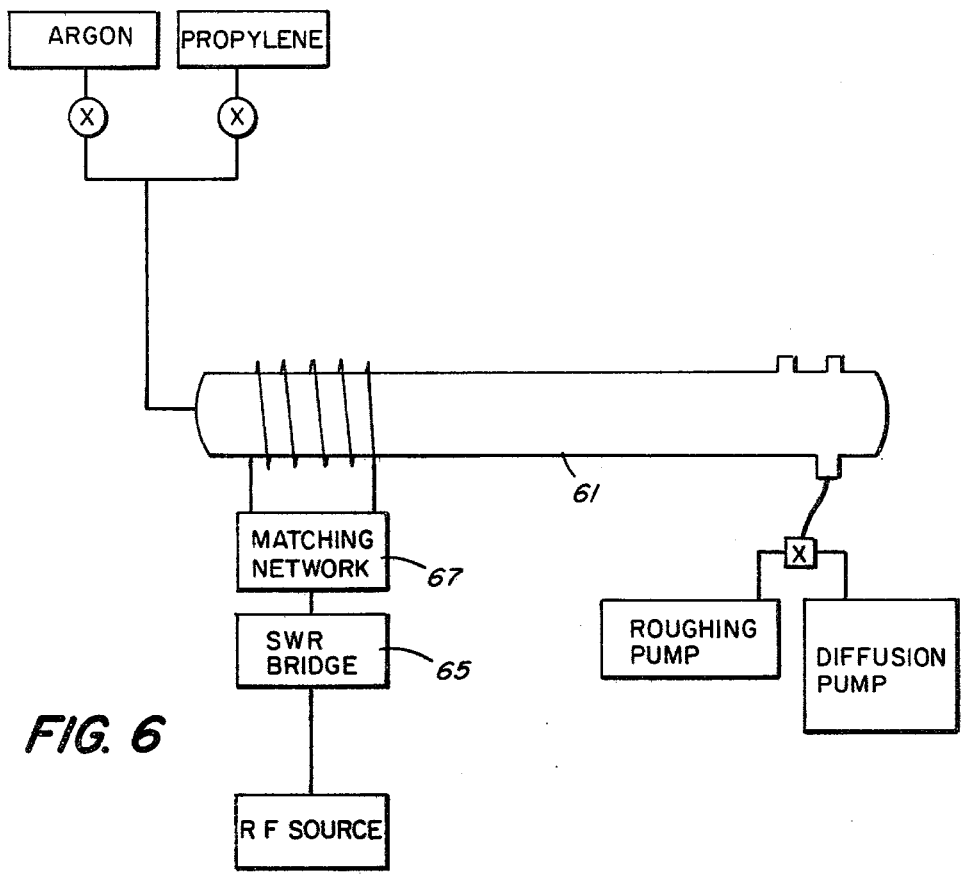
FIG. 6 is a diagram of an r.f. plasma polymerization apparatus employed in forming an in situ coating on the sensor of FIGS. 1 and 2.

The protective coating, described earlier as being applied over at least the front surface of the substrate 11, is formed in situ by plasma polymerization. After the reference electrode has been formed and the cathode has been sealed in the opening 43 and shaved flush with the face of the substrate, the substrates are placed in a vacuum chamber for the plasma forming process. In one particular implementation, illustrated in FIG. 6, a glass tube 61 about 75 millimeters in diameter and 100 centimeters long was utilized as the vacuum chamber. One end was connected to a vacuum pumping system and an r.f. coil 63 was placed around the other end. Provision was made at the end adjacent the coil for the bleeding in of selected gases.

In one particular device utilized, the coil was energized at 13.56 megahertz with about 100 watts of power. A conventional diathermy r.f. generator was used to power the coil through a conventional standing wave bridge 65 and matching network 67.

Substrates to be coated are placed within the tube 67 on glass slides. The vessel was then closed and evacuated to a pressure of about one micron. To effect cleaning and outgasing, an argon plasma is initially used. An argon flow of about 2.5 ccs per minute was introduced in the tube adjacent the RF zone, the pressure being held at about 35 microns. This condition is maintained for about 20 minutes.

Following the cleaning and after allowing the argon to be purged from the system, propylene monomer gas is bled into the system adjacent to the r.f. zone at a flow of about 0.75 sccm, yielding a pressure of about 6 microns. As is understood by those skilled in the art, the plasma discharge, created in the gas by the applied r.f. energy, creates bonding sites and permits an in situ r.f. energy polymerization of the monomer gas causing an intimate and tightly bonded coating to be formed on surfaces within the tube. With the particular apparatus utilized, the presently preferred coating is about 1.5 micrometers thick and is produced by operating the coating process for about 140 minutes.

Though operated in a heated mode, the sensor illustrated in FIG. 1 has a low enough power consumption that a feedback-controlled energizing circuit for the heater and calibrated polarographic current measuring circuit can all be battery operated and still provide a quite compact and portable unit. A suitable circuit is illustrated in the diagram in FIG. 7. This system incorporates batteries B1–B4 which directly provide plus and minus 9 volt unregulated supplies and a plus 18 volt unregulated supply. Regulators IC 6 and IC 7 provide regulated plus 5 and minus 5 volt supplies from the positive and negative 9 volt supplies, respectively.

In the sensing circuit, the input amplifier IC 1 is connected as a shunted integrator or a low pass filter to remove any high frequency artifacts from the signal obtained from the cathode 15. The cathode is connected directly to the inverting input of this amplifier while the reference electrode 17 is connected to ground. A reference potential, obtained from the divider string R7–R9, is applied to the non-inverting input of amplifier IC 1 and a portion of this reference voltage is applied to the non-inverting input of a second amplifier stage IC 2 through resistors R3 and R5. This second state is connected as a fixed gain amplifier.

The output signal from amplifier IC 2 is applied to a divider string R10–R12 which includes a potentiometer R11 allowing for an initial calibration or sensitivity setting. The output from this divider string is supplied to a digital volt meter, preferably driving a liquid-crystal digital display. The same signal is also applied to a voltage follower buffer amplifier IC 3 which provides an isolated signal, through an output jack J1, suitable for driving an external chart recorder or the like.

Figure 7:
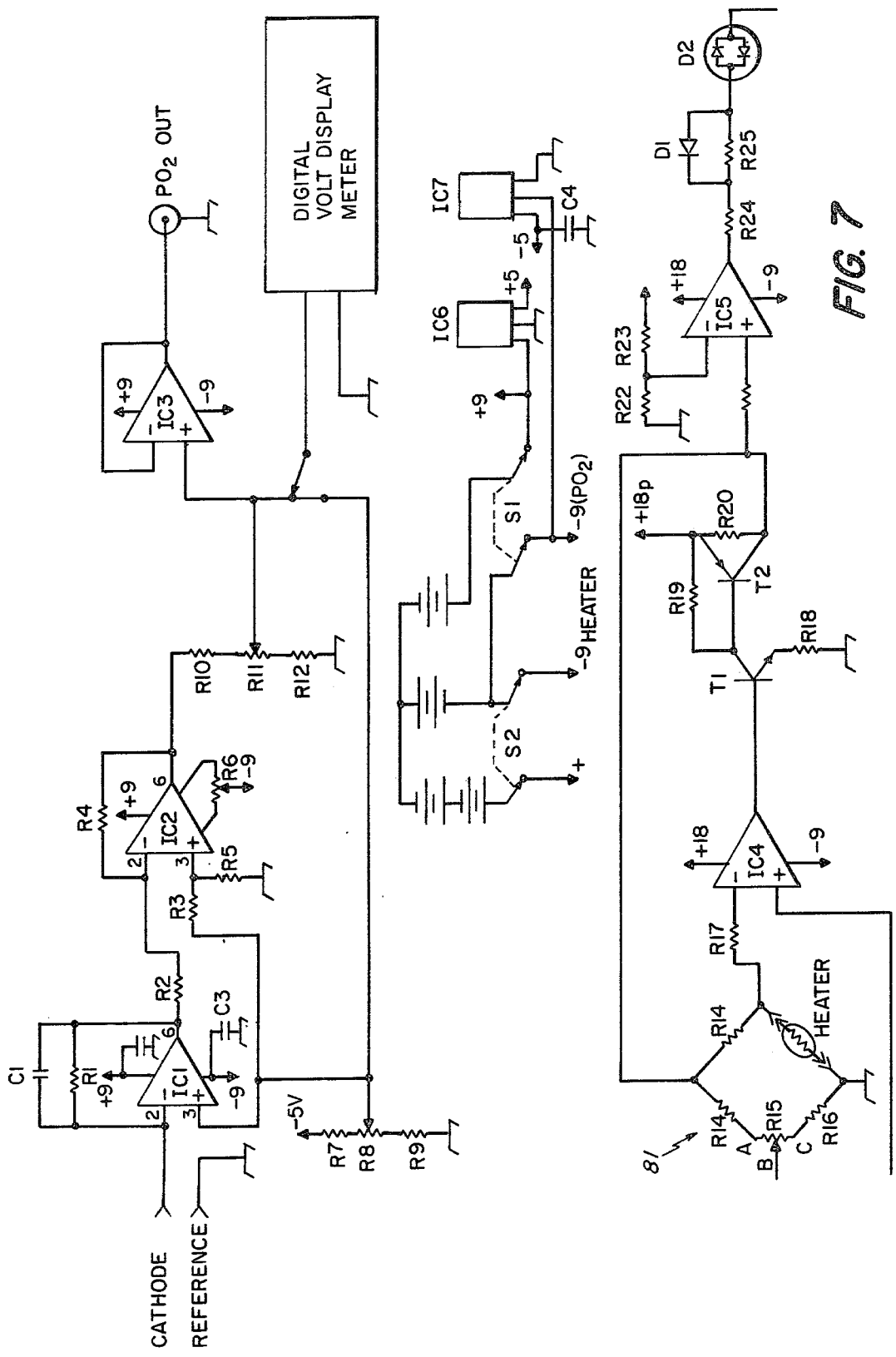
FIG. 7 is a schematic circuit diagram of temperature control and current sensing apparatus employed in conjunction with the sensor of FIGS. 1 and 2.

As has been indicated previously, the heater element 21 is constructed using a thermistor type paste so that its resistance varies as a function of temperature and it can be employed as both the sensing element and the output element of the feedback temperature controller. With reference to FIG. 7, the heater 17 is incorporated in a bridge circuit 81 where it is in series with a fixed resistor R13. This series current path forms one side of the bridge and is connected between ground and the output line 83 of the temperature controller. The value of resistor R13 is chosen, in relation to the nominal value of the heater 21, so that most of the power is dissipated in the heater.

The other arm of the bridge 81 comprises fixed resistors R14 and R16 and a potentiometer R15. Potentiometer R15 allows adjustment of the set point temperature. The junction between resistor R13 and the heater 21 is connected, through a resistor R17, to the inverting input of an amplifier IC 4 while the arm of the potentiometer R15 is connected to the non-inverting input of this amplifier. The output of amplifier IC 4 drives a power amplifier comprising a pair of transistors T1 and T2 of complementary conductivity types. The output signal of the power amplifier, taken from the collector of transistor T2, is applied back to the bridge as the output signal of the temperature controller. In this controller circuit, the amplifier IC 4 acts merely as a comparator and the entire circuit operates in a switching or "bang-bang" mode in which a form of duty-cycle modulation is obtained rather than an analogue or amplitude control.

The output signal is also applied to the non-inverting input of an amplifier IC 5, a reference voltage being applied to the non-inverting input. This amplifier drives, through a pair of resistors R24 and R25, a two-color light emitting diode D2. Diode D2 is the type which emits light of one color when driven in one direction and light of another color when driven in the opposite direction. Amplifier IC 5 is connected to both negative and positive supplies so as to provide a positive output signal when the heater is energized and a negative output signal when the heater is de-energized. Accordingly, when the temperature controller is operating in its duty cycle modulation mode, the diode will emit a light which is a mixture of the two colors and this indicates proper operation. If, however, due to some failure in the circuitry or in the connections to the sensor, the heater output signal is locked either high or low, the corresponding pure color of the diode will be generated indicating the malfunction.

Figure 8:
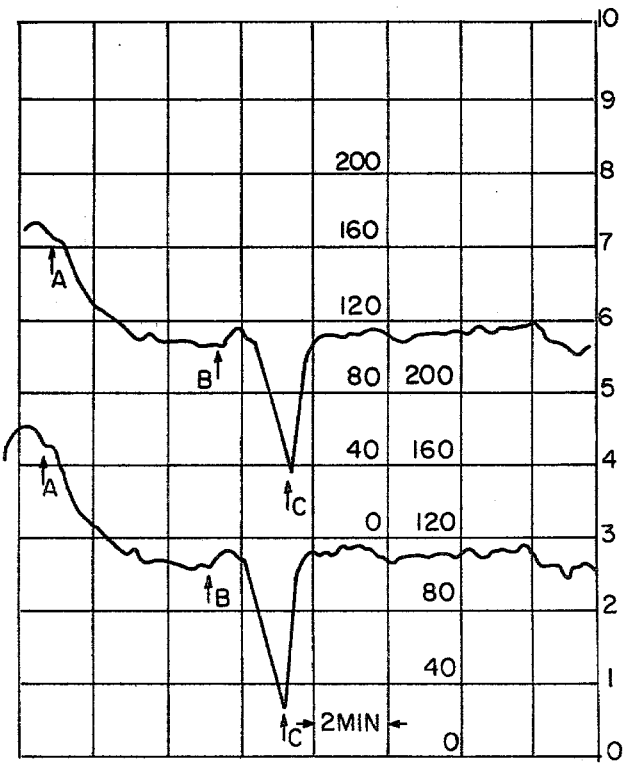
FIG. 8 is a graph representing the operation of a system constructed in accordance with the invention.

FIG. 8 represents recordings of the output signals obtained from two different transcutaneous oxygen sensors applied to the forearm of an adult male. The upper curve represents a reading obtained from commercial apparatus utilizing a Clark type electrode, whereas the bottom curve illustrates the response of the particular system described herein. The portion of the test reproduced includes a period, indicated by the reference character A where the subject is breathing essentially pure oxygen; a subsequent period, indicated by reference character B, where the subject was breathing normal room air; and a period, indicated by reference character C, where the subject held his breath for as long a period as practical. The curves illustrate that the much simpler solid state sensor of the present invention yielded results which are at least comparable to those obtained with the much more cumbersome and difficult to use Clark type electrode. In fact, in most instances, it seems to provide a faster response to abrupt changes in state.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

I claim:

1. Apparatus for measuring the oxygen content of a patient's blood, said apparatus comprising:
   a thin flat substrate having front and back surfaces, the front surface being adapted to contact a patient's skin;

a noble metal cathode extending through said substrate from the back surface to the front surface where a limited area is exposed;
on said front surface, silver/silver chloride reference electrode;
printed onto the back surface of said substrate, a resistor for heating said substrate;
over at least the front surface of said substrate with said electrodes, a coating of an in situ plasma polymerized coating;
feedback-controlled means for energizing said resistor to heat said substrate to a predetermined temperature suitable for producing hyperemia in the adjacent tissue of a patient to whom the front face of the substrate is applied; and
circuit means for applying a potential between said cathode and said reference electrode and for measuring the resultant current, the current so measured being a function of the oxygen content of the patient's blood.

2. Apparatus for measuring the oxygen content of a patient's blood, said apparatus comprising:
a thin flat ceramic substrate having front and back surfaces, the front surface being adapted to contact a patient's skin;
a noble metal cathode extending through said substrate from the back surface to the front surface where a limited area is exposed for reducing oxygen;
on said front surface, a reference electrode comprising a sintered silver/silver chloride composite in a non-organic fusible binder;
printed onto the back surface of said substrate, a resistor for heating said substrate, the resistance of said resistor being variable as a function of temperature;
feedback-controlled means responsive to the resistance of said resistor for energizing said resistor to heat said substrate to a predetermined temperature suitable for producing hyperemia in the adjacent tissue of a patient to whom the front face of the substrate is applied; and
circuit means for applying a potential between said cathode and said reference electrode and measuring the resultant current, the current so measured being a function of the oxygen content of the patient's blood.

3. Apparatus for measuring the oxygen content of a patient's blood, said apparatus comprising:
a thin flat ceramic substrate having front and back surfaces, the front surface being adapted to contact a patient's skin;
a noble metal cathode extending through said substrate from the back surface to the front surface where a limited area is exposed for reducing oxygen;
on said front surface, a reference electrode comprising a composite of silver/silver chloride in a glass frit fusible binder;
printed onto the back surface of said substrate, a resistor for heating said substrate;
over at least the front surface of said substrate with said electrodes, a coating of in situ plasma polymerized polypropylene;
feedback-controlled means for energizing said resistor to heat said substrate to a predetermined temperature suitable for producing hyperemia in the adjacent tissue of a patient to whom the front face of the substrate is applied; and
circuit means for applying a potential between said cathode and said reference electrode and measuring the resultant current, the current so measured being a function of the oxygen content of the patient's blood.

4. Apparatus for measuring the oxygen content of a patient's blood, said apparatus comprising:
a thin flat ceramic substrate having front and back surfaces, the front surface being adapted to contact a patient's skin;
a thin gold wire extending through said substrate from the back surface to the front surface where an end thereof is exposed for reducing oxygen;
on said front surface, a reference electrode comprising a sintered silver/silver chloride composite in a glass frit fusible binder;
printed onto the back surface of said substrate, a resistor for heating said substrate;
over at least the front surface of said substrate with said electrodes, a coating of in situ plasma polymerized polypropylene.

5. Apparatus as set forth in claim 4 including a thermistor element which is also printed onto the back surface of said substrate.

6. Process for thick film manufacturing an oxygen sensing electrode comprising the steps of:
(A) providing a thin, thermally conductive electrically non-conductive refractory substrate having front and back surfaces;
(B) thick film screening onto said back surface of said substrate electrically conductive paste to form a plurality of conductive pads;
(C) firing said substrate to bond said conductive paste to said substrate;
(D) thick film screening a paste comprising a mixture of silver and silver chloride onto the front surface of said substrate to form a reference anode;
(E) firing said substrate to bond said silver and silver chloride paste to said substrate;
(F) providing a resistor paste;
(G) thick film screening said resistor paste onto said back side of said substrate to form an elongate heating element, the ends of said heater element resting on a pair of said conductive pads;
(H) firing said substrate to bond said resistor paste forming said heater element to said substrate;
(I) providing a noble metal cathode extending from one of said pads, through a hole in said substrate, to the front surface of said substrate; and
(J) connecting said reference electrode to another of said pads.

7. Process for thick film manufacturing an oxygen sensing electrode comprising the steps of:
(A) providing a thin, thermally conductive electrically non-conductive refractory substrate having front and back surfaces;
(B) thick film screening onto said back surface of said substrate electrically conductive paste to form a plurality of conductive pads;
(C) firing said substrate to bond said conductive paste to said substrate;
(D) thick film screening a paste comprising a mixture of silver and silver chloride together with a fusible glass frit onto the front surface of said substrate to form a reference anode;
(E) firing said substrate to fuse said glass frit and bond said silver and silver chloride to said substrate;
(F) providing a thermistor paste;

(G) thick film screening said thermistor paste onto said back side of said substrate to form an elongate heating element, the ends of said heater element resting on a pair of said conductive pads;
(H) firing said substrate to bond said resistor paste forming said heater element to said substrate;
(I) providing gold wire extending from one of said pads, through a hole in said substrate, to the front surface of said substrate;

(J) connecting said reference electrode to another of said pads; and
(K) by plasma polymerization, forming a coating of an oxygen permeable polymer over said front surface.

8. Process as set forth in claim 7 wherein the screening of said thermistor paste also provides an elongate thermistor element separate from said heater.

* * * * *